United States Patent [19]

Fujita et al.

[11] Patent Number: 4,594,426
[45] Date of Patent: Jun. 10, 1986

[54] BENZOXAZOLE DERIVATIVE INTERMEDIATES FOR SYNTHESIS OF DYE RELEASING REDOX COMPOUNDS

[75] Inventors: Shinsaku Fujita; Koichi Koyama; Yoshio Inagaki, all of Kanagawa, Japan

[73] Assignee: Fuji Photo Film Co., Ltd., Kanagawa, Japan

[21] Appl. No.: 225,820

[22] Filed: Jan. 16, 1981

[30] Foreign Application Priority Data

Jan. 17, 1980 [JP] Japan .................................. 55-4263

[51] Int. Cl.$^4$ ............................................ C07C 93/14
[52] U.S. Cl. .................................. 548/217; 564/413;
430/218; 430/223; 430/242; 430/380; 430/390;
430/543; 430/552; 430/559
[58] Field of Search ........................ 548/217; 564/413

[56] References Cited

U.S. PATENT DOCUMENTS

| | | | |
|---|---|---|---|
| 3,222,196 | 12/1965 | Davies et al. | 106/57 |
| 3,307,947 | 3/1967 | Idelson et al. | |
| 3,932,381 | 1/1976 | Haase et al. | 260/197 |
| 4,055,428 | 10/1977 | Koyama et al. | 96/73 |
| 4,070,529 | 1/1978 | Delmas et al. | 106/57 |
| 4,135,929 | 1/1979 | Fernandez et al. | 96/3 |
| 4,268,625 | 5/1981 | Fujita et al. | 430/562 |
| 4,336,322 | 6/1982 | Fujita et al. | 430/242 |

FOREIGN PATENT DOCUMENTS

| | | | |
|---|---|---|---|
| 51-54552 | 5/1976 | Japan . | |
| 5610179 | of 1979 | Japan | 548/22 |
| 7910 | of 1905 | United Kingdom | 564/413 |

OTHER PUBLICATIONS

Fuji Photo Film Co., Ltd., 80/153775, Jap. Chemical Abstract, 94: 175105f.
Barton et al, "The Synthesis & Reactions of Organic Compounds", vol. 4, 1979, 971-972.
McLamore, J. Amer. Chem. Soc., vol. 73, 1951, pp. 2225-2230.

Primary Examiner—George F. Lesmes
Assistant Examiner—S. A. Gibson
Attorney, Agent, or Firm—Sughrue, Mion, Zinn, Macpeak, and Seas

[57] ABSTRACT

Benzoxazole derivatives represented by general formula (I) which are intermediates for synthesis of o-sulfonamidophenol derivatives useful as dye releasing redox compounds in a color diffusion transfer color image forming process:

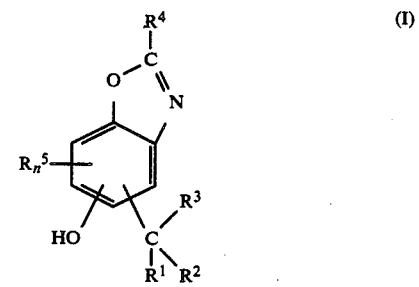

(I)

wherein $R^1$ and $R^2$, which may be the same as or different from each other, each represents an alkyl group or an aryl group or they may combine and form a ring; $R^3$ represents a hydrogen atom, an alkyl group or an aryl group; $R^4$ represents an alkyl group or an aryl group; $R^5$ represents an alkyl group, an alkoxy group, an alkylthio group, an arylthio group, a halogen atom or an acylamino group, or —$CR^1R^2R^3$ and $R^5$ may combine and form the nucleus

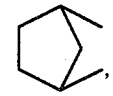

which is condensed at the 6- and the 7-positions of the benzoxazole nucleus; and n is 0, 1 or 2.

3 Claims, No Drawings

BENZOXAZOLE DERIVATIVE INTERMEDIATES FOR SYNTHESIS OF DYE RELEASING REDOX COMPOUNDS

BACKGROUND OF THE INVENTION

1. Field of the Invention

The present invention relates to intermediates for the synthesis of o-sulfonamidophenol derivatives useful as dye releasing redox compounds (abbreviated as DRR compounds hereinafter) and o-aminophenol derivatives useful as developing agents, both of which can be employed in color photography. More particularly, it is concerned with intermediates for the synthesis of o-sulfonamidophenol derivatives which release diffusible dyes by a redox reaction resulting from development processing of a silver halide.

2. Development of the Invention

In U.S. Pat. No. 4,076,529 there is described a color diffusion transfer color image forming process using DRR compounds. The term "DRR compound" as used therein means a p-sulfonamidophenol (or a p-sulfonamidonaphthol) compound in which a non-diffusible phenolic group (or naphtholic group) is bonded to a dye moiety via a sulfonamido group at its p-position.

However, our research found that the above-described p-sulfonamidophenols provide a sufficiently high density for a transferred image only with difficulty. Moreover, since the above-described p-sulfonamidonaphthols leave p-naphthoquinones in areas of a light-sensitive element and cause yellow stains even though the light-sensitive element has been submitted to desilvering processing after dye release, it is impossible to utilize the color image remaining on such areas of the light-sensitive element as negative or positive image.

In Japanese Patent Application (OPI) No. 113624/76, o-sulfonamidophenols substituted by alkoxyl groups at the 4-position(s) are described as DRR compounds. These compounds possess rather good properties, compared with conventional DRR compounds, but they need to be further improved in dye releasing ability.

In addition, o-sulfonamidophenols having alkoxyl groups and methyl groups at their 5- and 4-positions, respectively, are described as DRR compounds in Japanese Patent Application (OPI) No. 149328/78. However, further improvement upon the dye releasing ability is required of these o-sulfonamidophenols also.

SUMMARY OF THE INVENTION

Therefore, a first object of the present invention is to provide an intermediate for producing an o-sulfonamidophenol derivative which acts as a DRR compound and provides a transferred dye image having high optical density when used in a diffusion transfer process.

A second object of the present invention is to provide an intermediate for producing an o-sulfonamidophenol derivative which acts as a DRR compound and provides, in a light-sensitive element, a residual dye image with greatly reduced yellow stain.

A third object of the present invention is to provide an intermediate for producing an o-sulfonamidophenol derivative which acts as a DRR compound which releases a dye with high efficiency.

The above-described objects are attained with a compound represented by the following general formula (I):

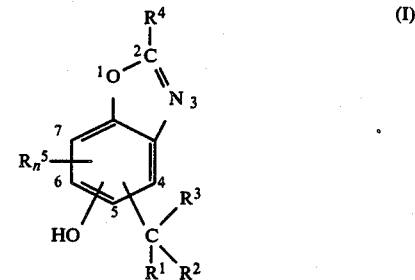

wherein $R^1$ and $R^2$ may be the same as or different from each other, and they each represent an alkyl or an aryl group, or they may combine to form a ring; $R^3$ represents a hydrogen atom, an alkyl group or an aryl group; $R^4$ represents an alkyl group or an aryl group; $R^5$ represents an alkyl group, an alkoxyl group, an alkylthio group, an arylthio group, a halogen atom or an acylamino group, or $R^5$ may be bonded to $-CR^1R^2R^3$ to form the nucleus of the structure,

which is condensed at the 6- and the 7-positions of the benzoxazole nucleus; and n is 0, 1 or 2.

DETAILED DESCRIPTION OF THE INVENTION

In the above-described general formula, the alkyl group represented by $R^1$ (and $R^2$ or $R^3$) has from 1 to 24, preferably from 1 to 17, more preferably from 1 to 10, and most preferably from 1 to 4, carbon atoms. It may be a straight chain, a branched or a cyclic alkyl group and further, may be substituted (such as an alkoxyl group, a cyano group, a hydroxy group, a halogen atom, a phenoxy group, a substituted phenoxy group, an acylamino group or so on). Preferred examples of the alkyl group represented by $R^1$ (and $R^2$ or $R^3$) include straight chain alkyl groups such as methyl, ethyl, propyl, butyl, pentyl, hexyl, heptyl, undecyl, pentadecyl, heptadecyl, etc.; and branched alkyl groups such as isopropyl, isobutyl, t-butyl, t-amyl, neopentyl, etc. Examples of the aryl group represented by $R^1$ (and $R^2$ or $R^3$) include a phenyl group, substituted phenyl groups, a naphthyl group and substituted naphthyl groups. Examples of the substituents of these substituted phenyl and napthyl groups include an alkoxy group, a cyano group, a hydroxy group, a nitro group, an alkyl group and so on. The ring formed by binding of $R^1$ to $R^2$ is preferably a 5- to 20-membered ring, preferably a 5- to 12-membered ring and most preferably a 6-membered ring. Specific examples of rings formed with $R^1$ and $R^2$ are those in which $R^1$ and $R^2$ are combined together to represent $-(CH_2)_x-$ wherein x is an integer of 4 to 19; of these, $-(CH_2)_x-$ wherein x is 5, 6, 7, 9 or 11 is preferred.

Unless otherwise indicated, the alkyl group or the alkyl moiety contained in, e.g., alkoxy, has 1 to 10 carbon atoms, preferably 1 to 4 carbon atoms and the acylamino group possesses 2 to 10 carbon atoms, preferably 2 to 4.

The alkyl group or the alkyl moieties of the alkoxyl group and the alkylthio group represented by $R^5$ have 1 to 40, preferably 1 to 24 and more particularly 1 to 4 carbon atoms. They may be straight chain, branched or cyclic, and may be substituted (e.g., alkoxy, cyano, hydroxy, halogen, phenoxy, substituted phenoxy, acylamino, etc.). As preferred examples of the alkyl group represented by $R^5$, mention may be made of those which are specifically described for $R^1$.

The arylthio group represented by $R^5$ is preferably phenylthio, a substituted phenylthio or a 1-phenyl-5-tetrazolylthio group, wherein the aryl moiety in the arylthio has 6 to 16 carbon atoms, preferably 6 to 10 carbon atoms, in total (including substituents, if present). Most preferably $R^5$ is a phenylthio or a substituted phenylthio.

Typical examples of the acylamino group represented by $R^5$ are an alkyl-CONH— group or a (substituted or non-substituted) phenyl-CONH— group. In this case the alkyl moiety in the alkyl-CONH— has 1 to 24 carbon atoms, preferably 1 to 17 carbon atoms.

As examples of the substituent in the substituted phenylthio or phenyl-CONH— group represented by $R^5$, mention may be made of those which are described as specific examples of the substituent contained in the substituted aryl group represented by $R^1$ or $R^2$.

Examples of the halogen represented by $R^5$ include fluorine, chlorine and bromine.

The alkyl group represented by $R^4$ contains 1 to 40, and preferably 1 to 24, carbon atoms. It may be straight chain, branched chain or cyclic. In addition, it may be substituted (e.g., alkoxy, cyano, hydroxy, halogen, phenoxy, substituted phenoxy, acylamino, etc.). Preferred examples of $R^1$ include straight chain alkyl groups such as a methyl group, an ethyl group, a propyl group, a butyl group, a pentyl group, a hexyl group, a heptyl group, an undecyl group, a pentadecyl group, a heptadecyl group and the like; and branched chain alkyl groups such as an isopropyl group, an isobutyl group, a t-butyl group, a t-amyl group, a neopentyl group and the like.

Examples of the aryl group represented by $R^4$ include phenyl group, substituted phenyl groups, naphthyl group, and substituted naphthyl groups. As examples of the substituents of these substituted phenyl and naphthyl groups, mention may be made of an alkoxy group, a cyano group, a hydroxy group, a nitro group, an alkyl group and so on. Of these groups, a methyl group is particularly preferred as $R^4$ from the standpoint of the facility of preparation.

In a preferred embodiment, the compound of the general formula (I) exhibits excellent effects in the case that the —OH group and the —$CR^1R^2R^3$ group present therein occupy the 6-position and the 5-position, respectively, or they occupy the 5-position and the 6-position, respectively, and $R^5$ is at the 4- and/or 7-position.

In a more preferred embodiment, the OH group and —$C(R^1)(R^2)(R^3)$ group are attached to the 6- and 5-positions, respectively, and $R^5$ attached to 4- and/or 7-position, that is, the compounds of the present invention are represented by the following general formula (II):

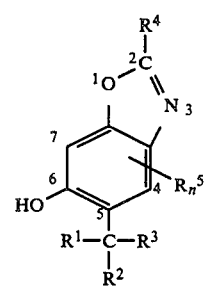

wherein $R^1$, $R^2$, $R^3$, $R^4$, $R^5$ and n have the same meanings as those substituents in the general formula (I).

More preferred compounds correspond to the case where $R^3$ in general formula (I) or (II) is an alkyl group or an aryl group as earlier defined.

Still more preferred compounds correspond to the cases where in general formula (I) or (II), $R^1$, $R^2$ and $R^3$ all are alkyl groups (which may be the same as or different from one another), n is 0 or 1 and $R^5$ is a lower alkyl group having 1 to 4 carbon atoms. Most preferred compounds are represented by the formula (II) wherein $R^1$, $R^2$ and $R^3$ all are alkyl groups having 1 to 24 carbon atoms (more preferably 1 to 17 carbon atoms). Therein, when n is 1, $R^5$ must be a lower alkyl group.

Specific examples of the compound of the present invention are illustrated below:

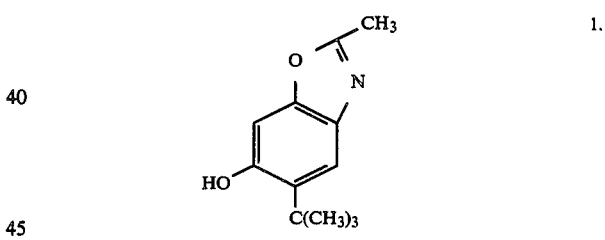

1.

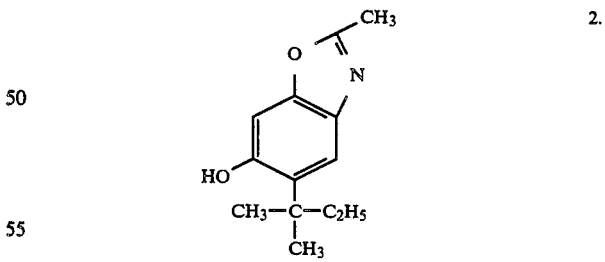

2.

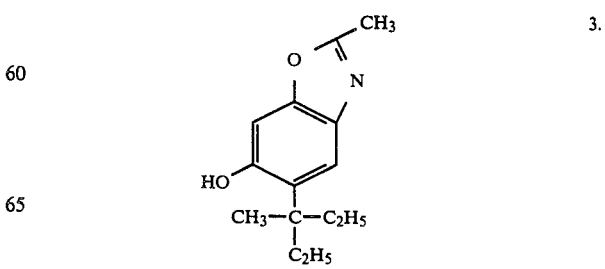

3.

4.
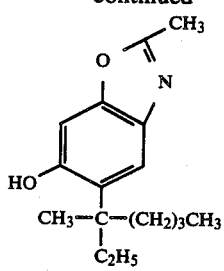

5.
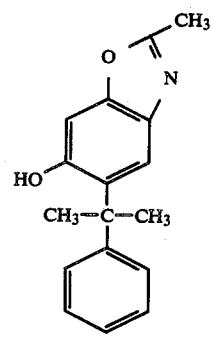

6.
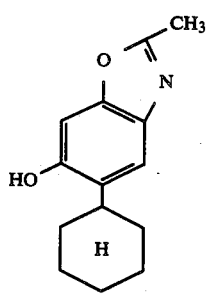

7.
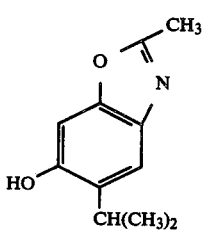

8.
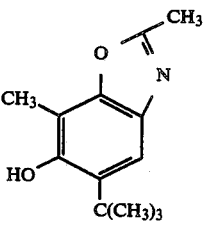

9.
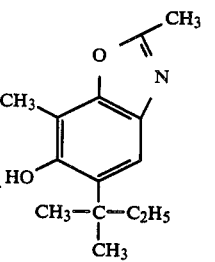

10.
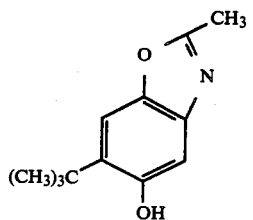

11.
(structure with $(CH_3)_2CH$ and $OH$)

12.
(bicyclic structure with $OH$)

Compound of formula (I) of the present invention can be synthesized by the following methods. The substituents $R^1$, $R^2$, $R^3$, $R^4$ and $R_n^5$ represent the same groups as in formula (I).

Method 1:

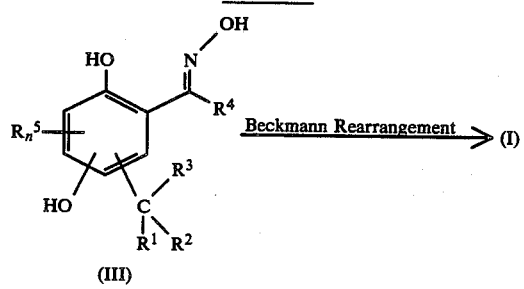

Method 2:

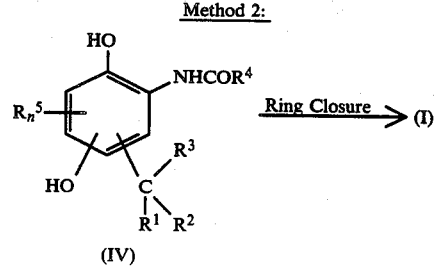

A detailed description of Method 1 is given below.

A benzoxazole (I) can be synthesized by allowing an oxime represented by the general formula (III) to react with phosphorus oxychloride in the presence of an amide represented by general formula (V)

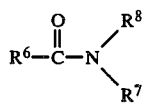

wherein $R^6$ represents a hydrogen atom or an alkyl group containing 1 to 23 carbon atoms; $R^7$ and $R^8$ may be the same as or different from each other, and they each represents an alkyl group having 1 to 24 carbon atoms; or $R^6$ and $R^7$, or $R^7$ and $R^8$ may combine with each other to form a ring.

The alkyl group represented by $R^6$ may be a straight chain or a branched chain alkyl group. The number of carbon atoms in such a group is 1 to 23, preferably 1 to 17 and, more particularly, 1 to 4. As examples of the alkyl group, mention may be made of a methyl group, an ethyl group, a propyl group, an isopropyl group, a butyl group and the like.

The alkyl group represented by $R^7$ or $R^8$ may be a straight chain or a branched chain alkyl group and it has 1 to 24, preferably 1 to 18 and, more particularly, 1 to 4 carbon atoms. For example it can be methyl group, ethyl group, propyl group, isopropyl group, butyl group or the like.

In addition, when $R^6$ and $R^7$, or $R^7$ and $R^8$ combine with each other to form a ring (preferably a 5- or a 6-membered ring), the ring formed may contain 1 to 2 hetero atoms (e.g., oxygen, nitrogen or sulfur) as constituent atom(s). In the case that $R^6$ and $R^7$ combine with each other, an amido linkage constitutes a part of the ring formed and, consequently, a ring having an oxy group, such as morpholine-3-one, pyrrolidone, caprolactam, piperidone, pyrrolidinone or the like, is formed. On the other hand, in the case that $R^7$ and $R^8$ combine with each other, the amido nitrogen becomes a member of the ring formed and therefore, a hetero ring such as morpholine, pyrrolidine, piperidine or the like is formed. Examples of such rings include for $R^6$-$R^7$:

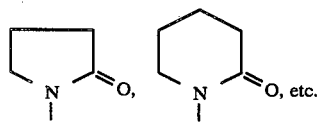

for $R^7$-$R^8$:

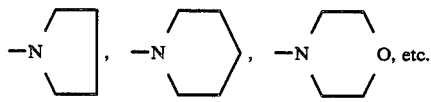

As the amide represented by the general formula (V), N,N-dimethylformamide, N,N-dimethylacetoamide and N-methylpyrrolidone are particularly favorable from the viewpoint that they are readily available and are inexpensive; they are miscible with water in all proportions and, therefore, after-treatment of the reaction solution can be done without difficulty; and they function as an excellent reaction solvent because of their high solubility to oxime (III).

In the above-described reaction, the amide represented by formula (V) functions as a catalyst in the process of the benzoxazole ring formation through Beckmann rearrangement. It is surmised that the amide of formula (V) complexes phosphorus oxychloride and the resulting complex accelerates the ring closure reaction from (III) to (I).

Method 1 of the present invention is carried out by allowing phosphorus oxychloride to react with the above-described oxime (III) in the presence of the amide (V). The reaction can be generally effected by a simple procedure where oxime (III) and amide (V) are mixed and then phosphorus oxychloride is added dropwise to the resulting mixture.

Depending on the solubility of oxime (III), the oxime may be dissolved in a solvent which does not have any influence on the reaction, for example, acetonitrile and a catalytic amount of amide (V) may be added thereto. Typically, the amount of solvent is from 1 to 1,000 parts by weight, preferably from 1 to 100 parts by weight, and more preferably from 1 to 50 parts by weight, per 1 part by weight of the oxime.

To the thus prepared solution, phosphorus oxychloride is added dropwise. However, the use of a large amount of amide (V)—both as a solvent and a catalyst—is superior to the use thereof in a catalytic amount from the standpoint of simplicity of procedure. In addition, phosphorus oxychloride may be dissolved in a solvent having no influence on the reaction (e.g., acetonitrile, tetrahydrofuran, acetone, sulforan, etc.), and the resulting solution then be added to the above-described mixture of the oxime (II) and the amide (V); or the phosphorus oxychloride may be added as it is without dissolving it in any solvent. The amount of the solvent used for dissolving phosphorus oxychloride is thus generally in a range of 0 to 100, preferably 0 to 50 parts by weight, per 1 part by weight of phosphorus oxychloride; wherein "0" means a case where no solvent is used and accordingly phosphorus oxychloride is dropwise added as is without dilution.

The amount of amide (V) to be used in the Method 1 of the present invention does not have any upper limit for the above-described reason. Therefore, amide (V) is basically used in a catalytic amount or more, more specifically, in an amount of about 0.01 mol or more, preferably about 0.1 mol or more and particularly about 1 mol or more, to 1 mol of oxime (III).

In Method 1 of the present invention, phosphorus oxychloride is used in an amount of about 0.3 to 20 mols, preferably about 0.3 to 5 mols, per 1 mol of oxime (III).

Since the above-described reaction proceeds quickly at a low temperature, the reaction temperature is not restricted to any special range. However, it is desirable that the reaction temperature is set within the range of about −78° C. to about 200° C., preferably about 0° to 100° C., more particularly, about 0° to 40° C. In the event that the reaction of the present invention is exothermic and the temperature of the reaction system rises beyond 40° C., the reaction system should be cooled so that the reaction temperature is maintained within the above-described temperature range. In particular, on the occasion that $R^6$ in the amide (V) is hydrogen, the temperature of the reaction system must be maintained at a temperature of 40° C. or lower in order to prevent side reactions from occurring.

The reaction is usually run at ordinary pressure, but it can be also conducted under increased pressure or reduced to a small extent, i.e., reduced pressure is from 1 to 760 mg/Hg, preferably 10–760 mg/Hg, and elevated pressure: 1–50 kg/cm², preferably 1–10 kg/cm²; most preferred is normal pressure.

The time spent in dropwise adding phosphorus oxychloride is selected depending upon the reaction temperature, the kind of the oxime used as a starting material, the reaction scale and so on. As indicated above, the reaction is exothermic, and in the event that the temperature rises higher than a certain maximum temperature, e.g., about 40° C. (optimum reaction temperature depends upon compounds used), undesired side-reactions might occur. Thus, the addition rate of phosphorus oxychloride is controlled such that the temperature does not exceed the maximum temperature, which would in turn regulate the time spent in the dropwise addition of phosphorus oxychloride. Usually, it is set within the range of about 30 minutes to about 3 hours. At the conclusion of the dropwise addition of phosphorus oxychloride the reaction proceeds in an instant and goes to completion in most cases. By way of precaution, the reaction system may be left for additional 30 minutes to 2 hours as it is and the reaction thereby terminated.

After the reaction is completed, the reaction mixture is usually cooled to room temperature by being allowed ty stand for time and, then, poured into ice water. By this treatment, a precipitate separates out. The resulting precipitate is filtered off and is recrystallized from a proper solvent such as benzene, alcohol or the like in a conventional manner. Thus, the desired benzoxazole (I) is obtained.

In the above-described purification of the reaction product, an operation where the contents are poured into ice water are neutralized with a proper alkali, e.g., sodium acetate, sodium bicarbonate, sodium carbonate, sodium hydroxide, etc., whereby the resulting solution comes to have a pH value of about 4 to about 7, may be further added with the intention of improving filtering efficiency regarding the filtration of precipitates and discharging the filtrate in a safe form.

The Beckmann rearrangement for the conversion of (III) into (I) proceeds even in the presence of a hydrogen chloride-acetic acid mixture and also using a Lewis acid, a Bronsted acid, an acid anhydride or an acid halide in the place of phosphorus oxychloride in the presence of the amide of formula (V).

The above-described Lewis acid used in combination with the amide of formula (V) is represented by the general formula (A):

$$A—X \qquad (A)$$

wherein A is a Lewis acid group and X is a halogen atom, particularly chlorine or bromine.

As examples of the Lewis acid which functions effectively as the Lewis acid of the present invention, mention may be made of:

Sulfur atom-containing Lewis acids:

$$Y^1—SO—X \qquad (Aa)$$

wherein $Y^1$ represents a halogen atom, or an unsubstituted or substituted phenyloxy group and X represents a halogen atom;

$$Y^2—SO_2—X \qquad (Ab)$$

wherein $Y^2$ represents an alkyl group, an unsubstituted or substituted phenyl group or a halogen atom; and X represents a halogen atom;

Phosphorus atom-containing Lewis acids:

$$Y_2{}^3—PO—X \qquad (Ac)$$

$$Y_2{}^3—P—X \qquad (Ad)$$

$$Y_4{}^3—P—X \qquad (Ae)$$

wherein $Y^3$ and X each represents a halogen atom, and it is preferable for them to represent the same halogen atom; and Carbon atom-containing Lewis acids:

$$Y^4—CO—X \qquad (Af)$$

wherein $Y^4$ represents an unsubstituted or substituted phenyloxy group, a halogen atom or X—CO— where X represents a halogen atom.

Examples of the substituent of the substituted phenyl group represented by $Y^1$ include a halogen atom, preferably Cl or Br, nitro group, cyano group, an alkoxy group, an alkyl group and so on.

The halogen atom represented by $Y^1$ is chlorine or bromine.

The alkyl group represented by $Y^2$ contains 1 to 8, preferably 1 to 4, carbon atoms, and it may be a straight chain or a branched chain alkyl group and further may be a cyclic alkyl group. The most preferable alkyl group represented by $Y^2$ is a methyl group.

Examples of the substituent of the substituted phenyl group represented by $Y^2$ include a halogen atom, particularly chlorine, nitro group, cyano group, an alkoxy group, an alkyl group and so on.

Representative of the halogen atoms represented by $Y^3$ are chlorine and bromine.

Examples of the substituent of the substituted phenyloxy group represented by $Y^4$ include a halogen atom, particularly chlorine, nitro group, cyano group, an alkoxy group, an alkyl group and so on.

A particularly favorable example of the halogen atom represented by $Y^4$ is chlorine.

Specific examples of the Lewis acid which can be used in a still more preferred embodiment of the present invention are thionyl chloride ($SOCl_2$) when selected from those represented by formula (Aa); methanesulfonyl chloride ($CH_3SO_2Cl$), p-toluenesulfonyl chloride, p-chlorobenzenesulfonyl chloride, m- and p-nitrobenzenesulfonyl chlorides and sulfuryl chloride ($SO_2Cl_2$) when selected from those represented by formula (Ab); $POCl_3$ and $POBr_3$ when selected from those represented by formula (Ac); $PCl_3$ and $PBr_3$ when selected from those represented by formula (Ad); $PCl_5$ when selected from those represented by formula (Ae); phenyl chloroformate when selected from those represented by formula (Af); phosgene and oxalyl chloride; and so on.

The Lewis acid method of synthesis can generally be effected by a simple procedure where oxime (III) and amide (V) are mixed and then the Lewis acid (A) is dropped into or added to the resulting mixture. Depending on the solubility of oxime (III), the oxime may be dissolved in a solvent having no influence on the reaction, such as acetonitrile or the like, and the amide added thereto. To the resulting solution, the Lewis acid is dropwise added. Amide (V) may be added in a large amount both as a reacting species and a solvent. In addition, the Lewis acid (A) may be dissolved in a solvent having no influence on the reaction and the resulting solution then be added to the above-mentioned mixture or the Lewis acid (A) may be added as is.

The amount of amide (V) to be used in the present invention does not have any upper limit for the above-described reason. Therefore, amide (V) is used basically in a catalytic amount or more, and, specifically, in an amount of about 0.001 mol or more, preferably about 0.01 mol or more and, particularly, about 1 mol or more, per 1 mol of the oxime (III). I.e., reduced pressure is from 1 to 760 mg/Hg, preferably 10 to 760 mg/Hg, and elevated pressure is from 1 to 50 kg/cm$^2$, preferably 1 to 10 kg/cm$^2$; most preferred is normal pressure.

The amount of Lewis acid (A) used in the present invention is generally within the range of about 0.3 to 20 mols, preferably within the range of about 0.3 to 5 mols and, more particularly, within the range of about 1 to 5 mols, per 1 mol of oxime (III). As indicated above, the reaction is exothermic, and in the event that the temperature rises higher than a certain maximum temperature, e.g., about 40° C. (optimum reaction temperature depends upon compounds used), undesired side-reactions might occur. Thus, the addition rate of phosphorus oxychloride is controlled such that the temperature does not exceed the maximum temperature, which would in turn regulate the time spent in the dropwise addition of phosphorus oxychloride.

Since the above-described reaction of the present invention proceeds quickly at a low temperature under ordinary circumstances, there is no special limit to the reaction temperature. However, it is desirable that the reaction temperature be set within the range of about −78° C. to about 200° C., preferably about 0° C. to about 100° C. and, more particularly, about 0° C. to about 40° C. In the event that the reaction is an exothermic reaction and the temperature of the reaction system rises beyond 40° C., the reaction system should be cooled and maintained at a temperature within the above-described range. In particular, on the occasion that $R^6$ in amide (V) is hydrogen, the temperature of the reaction system must be maintained at a temperature not higher than 40° C. in order to prevent side reactions from occurring. Contrary to the above, the reaction system may be heated to accelerate the reaction in the case that $R^6$ is an alkyl group.

The reaction is usually run under an ordinary pressure, but it can be also conducted under increased pressure or reduced to a small extent.

The time spent in dropping or adding Lewis acid (A) is selected depending upon the reaction temperature, the kind of the oxime used as a starting material, the reaction scale and so on. Usually, it can be set within the range of about 30 minutes to about 3 hours. In most cases, at the conclusion of the dropping or adding procedure, the reaction proceeds in an instant and goes to completion. By way of precaution, the reaction system may be left for additional 30 minutes to 2 hours as it is, whereby the reaction is terminated completely.

After the reaction is completed, the reaction mixture is usually cooled to room temperature by being allowed to stand for a time and, then, poured into ice water. By this treatment, a precipitate separates out. The resulting precipitate is filtered off and is recrystallized from a proper solvent such as benzene, an alcohol or so on. Thus, the desired benzoxazole (I) is obtained.

To the above-described separation steps, an operation where the reaction contents poured into ice water are neutralized with an appropriate alkali, e.g., sodium acetate, sodium bicarbonate, sodium carbonate, sodium hydroxide, etc., whereby the resulting solution comes to have a pH value of about 4 to about 7, may be added for the purposes of improvement of filtering efficiency of the precipitates and safe discharge of the filtrate.

In accordance with the method for synthesis in the present invention wherein a Lewis acid and an amide are used as reacting agents, benzoxazole derivatives can be obtained in high yield under mild reaction conditions and through a simple procedure. Further, even oximes which are subject to decomposition at high temperatures (for example, 2,5-dihydroxyacetophenone oxime derivatives) can be employed as a starting material because the reaction proceeds at a low temperature. Therefore, the synthesis method of the present invention is very useful.

The ring closure reaction of above Method 2 can be effected by working up the compound of rormula (IV) in the presence of an acid catalyst such as p-toluenesulfonic acid where p-toluenesulfonic acid us used in an amount of 0.01 mol to 1 mol, preferably 0.1 mol to 0.3 mol, per 1 mol of the compound represented by formula (IV).

The solvent employed for the reaction is selected depending upon the solubility of the compound of formula (IV) therein. The solvent is generally used in an amount of from 1 to 1,000, preferably from 1 to 100, and more preferably from 1 to 50 parts by weight, per 1 part by weight of (IV). Examples of such a solvent include aromatic hydrocarbon series solvents, e.g., benzene, toluene, xylene, etc.; alcohol series solvents, e.g., ethanol, n-butanol, isopropyl alcohol, etc.; halogenated hydrocarbon series solvents, e.g., 1,1,1-trichloroethane, 1,2-dichloroethane, etc.; and ester series solvents, e.g., ethyl acetate, etc. The reaction temperature is set within the range of about 0° C. to about 200° C., preferably about 50° C. to 150° C. The reaction time is usually set within the range of about 1 hour to about 24 hours. I.e., reduced pressure is from 1 to 760 mg/Hg, preferably 10 to 760 mg/Hg, and elevated pressure is from 1 to 50 kg/cm$^2$, preferably from 1 to 10 kg/cm$^2$; most preferred is normal pressure.

The ring closure reaction of Method 2 can also be conducted using the combination of phosphorus oxychloride with amide (V) as a reacting agent. Namely, benzoxazole (I) can be produced by the reaction of the compound represented by formula (IV) with phosphorus oxychloride in the presence of the amide represented by formula (V). In general, benzoxazole (I) can be synthesized by the simple procedure that compound (IV) and amide (V) are mixed and phosphorus oxychloride is added dropwise thereto. Preferred addition amounts of phosphorus oxychloride, reaction temperatures, reaction times, solvents and after-treatment methods are the same as those hereinbefore described for Method 1.

Oxime (III) which is the starting material in Method 1 can be synthesized by the following process:

Process I

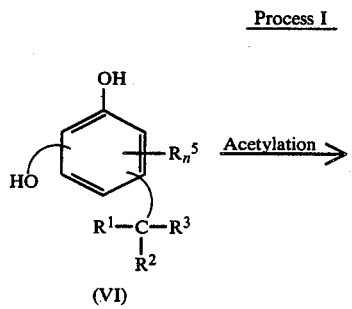

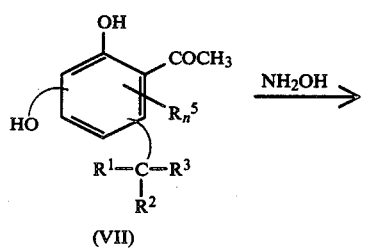

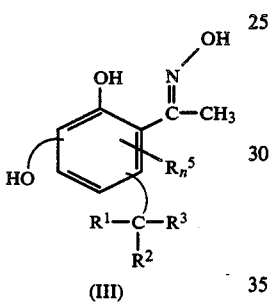

In Process I, the compound represented by formula (VI) is subjected to acetylation of its nucleus, for example, by the combined use of BF$_3$ and acetic acid to obtain compound (VII) and then resulting compound (VII) is reacted with hydroxylamine to produce oxime (III). Source compound (VI) is commercially available.

A representative method for the synthesis of compounds represented by formula (IV) is illustrated below using an easy to scan reaction scheme. Specifically, the reaction process is described using as a representative example resorcinol derivative (IV'). However, the positions of the OH substituent, the —R$_n^5$ substituent and the —CR$^1$R$^2$R$^3$ substituent are not intended to be construed as being limited to those in this example.

Process II

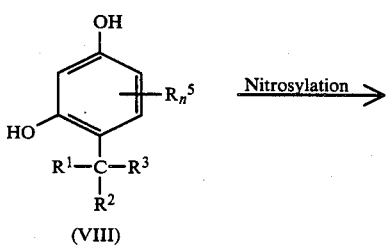

-continued
Process II

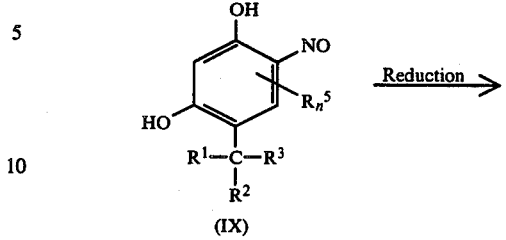

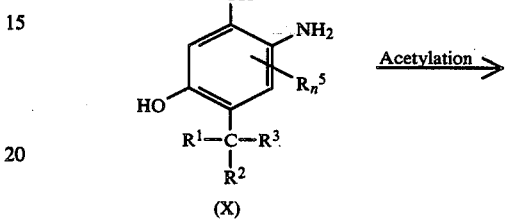

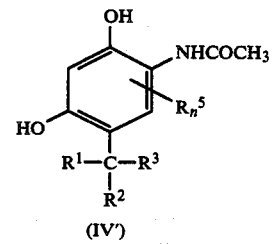

The description of Process II is as follows: resorcinol derivative (VIII) is subjected successively to nitrosylation, reduction and acetylation to result in conversion into compound (IV'). Other derivatives of formula (IV), i.e., catechol type (o-dehydroxy type), hydroquinone type (p-dehydroxy type), can be prepared by subjecting catechol or hydroquinone type compounds corresponding to (VIII) (wherein only a relative position of two OH groups is different) to acetylation, nitration, reduction and an acid treatment, in turn, in a conventional manner to obtain compound (IV). Each of these steps can be practiced using the procedure for the preparation of 2-acetoamido-4-cyclohexylresorcinol using 4-cyclohexylresorcinol as a starting material as described in W. M. McLamore, *J. Amer. Chem. Soc.*, Vol. 73, pp. 2225–2230 (1951). Source compound (VIII) is commercially available.

The compounds of this invention can be used in various photographic elements, as described, e.g., in U.S. Pat. No. 4,076,529, and in *Research Disclosure*, No. 151, 15162, November 1976.

A preferred process for producing a photographic transfer image in color using these compounds comprises the steps of:

(1) Treating an imagewise exposed photosensitive element of the invention with an alkaline processing composition in the presence of a silver halide developing agent to reflect development of the silver halide emulsion layers as a function of exposure, thereby oxidizing the developing agent and the oxidized developing agent in turn cross-oxizing the dye redox releasing compound;

(2) Forming an imagewise distribution of diffusible released dye as a function of the development of the silver halide emulsion layers by cleaving, under alkaline conditions, cross-oxidized dye redox releasing compounds; and (3) Diffusing out of the layer in which the dye redox releaser was coated at least a portion of the imagewise distributions of diffusible released dye.

Typical examples of some of the compounds of the present invention are illustrated in detail below.

EXAMPLE 1

Synthesis of Compound 1

In a mixture of 30 ml of N,N-dimethylacetamide and 30 ml of acetonitrile was dissolved 11 g of 5'-t-butyl-2',4'-dihydroxyacetophenone oxime. To the resulting solution, which was cooled on an ice bath with stirring, was dropwise added 20 ml of phosphorus oxychloride over a period of 30 minutes. The reaction mixture continued to be stirred for an additional 30 minutes as it was and, then, 200 mol of ice water was gradually added thereto over a period of an hour. The crystals thus precipitated were recovered by filtration, and 50 g of 5-t-butyl-2-methyl-6-benzoxazolol (Compound 1) was obtained. Yield 85%, Melting Point 264° to 266° C.

EXAMPLE 2

Synthesis of Compound 2

In the same manner as described in Example 1 except that 5'-t-amyl-2',4'-dihydroxyacetophenone oxime was used in place of 5-t-butyl-2,4-dihydroxyacetophenone oxime, 5-t-amyl-2-methyl-6-benzoxazolol (Compound 2) was obtained. Yield 62%, Melting Point 237° to 238° C.

EXAMPLE 3

Synthesis of Compound 3

In the same manner as described in Example 1 except that 2',4'-dihydroxy-5'-(1-ethyl-1-methylpropyl)acetophenone oxime was used in place of 5'-t-butyl-2',4'-dihydroxyacetophenone oxime, 5-(1-ethyl-1-methylpropyl)-6-benzoxazolol (Compound 3) was obtained. Yield 87%, Melting Point 217° to 218° C.

EXAMPLE 4

Synthesis of Compound 8

In the same manner as described in Example 1 except that 5'-t-butyl-2',4'-dihydroxy-3'-methylacetophenone oxime was used in place of 5-t-butyl-2,4-dihydroxyacetophenone oxime, 5-t-butyl-2,7-dimethyl-6-benzoxazolol (Compound 8) was obtained. Yield 85%, Melting Point 166° to 168° C.

EXAMPLE 5

Synthesis of Compound 10

In the same manner as described in Example 1 except that 2-acetyl-5-t-butylhydroquinone oxime was used in place of 5'-t-butyl-2',4'-dihydroxyacetophenone oxime, 6-t-butyl-2-methyl-5-benzoxazolol (Compound 10) was obtained. Yield 88%, Melting Point 203° to 205° C.

EXAMPLE 6

Synthesis of Compound 12

In the same manner as described in Example 1 except that 2-acetyl-5,8-methano-5,6,7,8-tetrahydro-1,4-naphthohydroquinone oxime was used in place of 5'-t-butyl-2',4'-dihydroxyacetophenone oxime, Compound 12 was obtained. Yield 89%, Melting Point 259° to 260° C.

EXAMPLE 7

In the same manner as described in Example 1 except that thionyl chloride was used in place of phosphorus oxychloride, Compound 1 was obtained with a yield of 80%.

EXAMPLE 8

In the same manner as described in Example 1 except that methanesulfonyl chloride was used in place of phosphorus oxychloride, Compound 1 was obtained with a yield of 72%.

EXAMPLE 9

In the same manner as described in Example 1 except that phenyl chloroformate was used in place of phosphorus oxychloride, Compound 1 was obtained with a yield of 75%.

EXAMPLE 10

In the same manner as described in Example 1 except that oxalyl chloride was used in place of phosphorus oxychloride, Compound 1 was obtained with a yield of 80%.

EXAMPLE 11

In the same manner as described in Example 6 except that thionyl chloride was used in place of phosphorus oxychloride, Compound 12 was obtained with a yield of 86%.

EXAMPLE 12

In the same manner as described in Example 1 except that 2',5'-dihydroxy-6'-t-butylacetophenone oxime and thionyl chloride were used instead of 5'-t-butyl-2',4'-dihydroxyacetophenone oxime and phosphorus oxychloride, respectively, the desired 2-methyl-5-hydroxy-6-t-butylbenzoxazolol was obtained. Yield 83% (light brown needles), Melting Point 203° to 205° C.

COMPARATIVE EXAMPLE

A mixture consisting of 3 g of 2,5-dihydroxy-3,4-dimethylacetophenone oxime and 12 ml of formic acid was refluxed for 3 hours. However, 2,6,7-trimethyl-5-hydroxybenzoxazole was not produced at all. The experiment discussed hereinabove was a duplication of Japanese Patent Application (OPI) No. 54552/76.

DRR compounds useful in a color diffusion transfer process can be synthesized using the compounds of the present invention as intermediates. Representative DRR compounds are the compounds represented by the following general formula (XI):

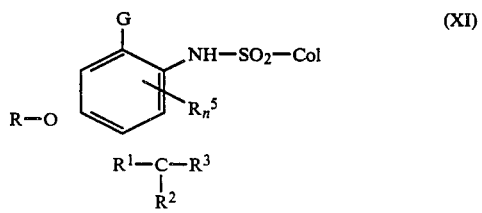

wherein $R^1$, $R^2$, $R^3$, $R^5$ and n have the same meanings as in the formula (I), respectively; G represents hydroxy group or a group capable of providing a hydroxy group by hydrolysis; Col represents a dye (e.g., cyan, magenta or yellow dye) residue or a dye precursor residue; and R represents an alkyl group or an aryl group, which is preferably a ballast group.

Specific examples of G include a hydroxy group; groups represented by the formula, alkyl-COO-, wherein 2 to 40, preferably 2 to 8, and more particularly, 2 to 4, carbon atoms are contained (e.g., acetoxyl, propionyloxy, etc.); and aromatic carbonyloxy groups having 6 to 40, preferably 6 to 15, and more particularly, 6 to 9, carbon atoms (e.g., benzoyl, substituted benzoyls, etc.).

Examples of Col include azo dye residues, azomethine dye residues, indoaniline dye residues, indophenyl dye residues, triphenylmethane series dye residues, anthraquinone dye residues, indigo series dye residues and their metal complex salt residues. In addition, Col includes those compounds which can produce the above-described dye residues by hydrolysis; for example, dye Japanese Patent Application No. 125818/73 (corresponding to OPI No. 78327/75, U.S. Pat. Nos. 3,222,196 and 3,207,947.) See also Japanese Patent Application (OPI) Nos. 33826/73, 114424/74, and 126332/74.

As compared with conventional DRR compounds, DRR compounds having general formula (XI) which are obtained using the compounds of the present invention possess the following advantages:

(i) They release dyes with high efficiency and, therefore, the amount used can be reduced.

(ii) Accordingly, the thickness of a layer containing the DRR compound can be reduced and the time required for image finishing can be shortened.

(iii) As a consequence of the decrease in the amount used, the amount of alkali and developing agent contained in a processing solution can be decreased.

(iv) As a consequence of the decrease in the amount used, an amount of a color-mixing preventing agent incorporated into an interlayer can be reduced. This leads to thinning of the interlayer thickness and contributes to shortening image finishing time.

(v) As a consequence of the decrease in the amount used, the amount of a dispersing solvent can be reduced.

(vi) As a consequence of the decrease in the amount used, the amount of silver halide emulsion can be reduced. This leads to a thinning of the emulsion layer and contributes to shortening the image finishing time.

(vii) They can provide sufficiently high transferred image density ($D_{max}$) and sufficiently low $D_{min}$.

(viii) Gradation of foot part is hard and, therefore, they are used to advantage in view of color reproducibility.

Further, of the DRR compounds having general formula (XI) those which have such the particular configuration where the $R^1R^2R^3C-$ group occupies the 4-position and the R—O— group occupies the 5-position to the substituent G are of great importance and have the following advantages, as compared with DRR compounds having the configuration where the $R^1R^2R^3C-$ group occupies the 5-position and the R—O— group occupies the 4-position:

(ix) The former DRR compounds can be used in combinations with developing agents having lower half-wave potentials (and consequently, higher developing speeds). Therefore, image forming time can be shortened.

(x) The former DRR compounds crystallize and separate out of their solutions more slowly. Therefore, emulsions containing the former DRR compounds have high stabilities.

Particularly favorable DRR compounds obtained by the use of the intermediates of the present invention are represented by the following general formula (XII):

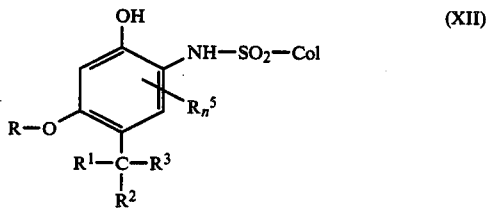

wherein $R^1$, $R^2$, $R^3$, R, $R^5$, n and Col have the same meanings as in formula (XI).

Specific examples of the DRR compound represented by the general formula (XI) are illustrated below.

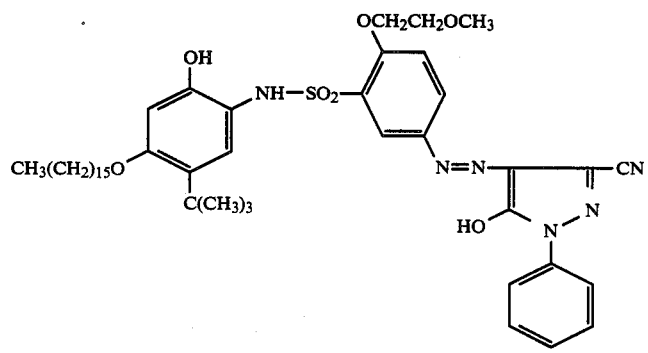

DRR-1

-continued
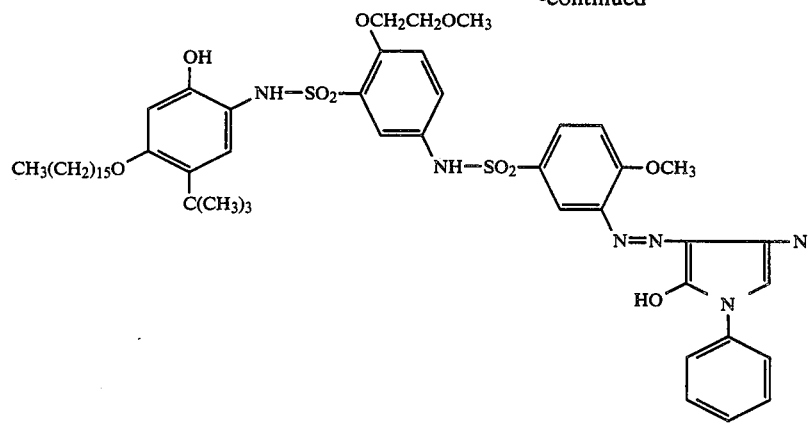 DRR-2
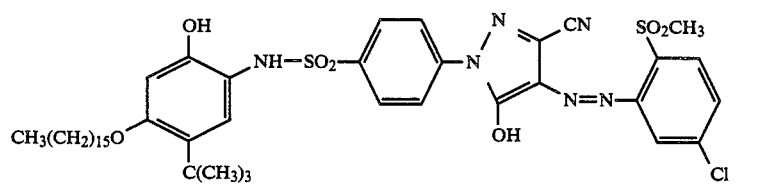 DRR-3
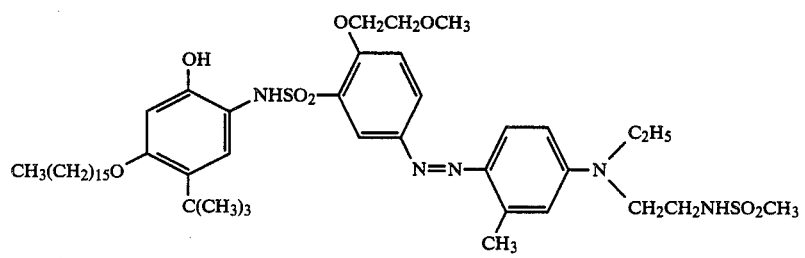 DRR-4
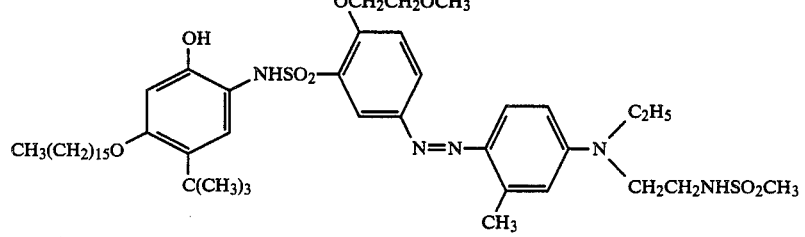 DRR-5
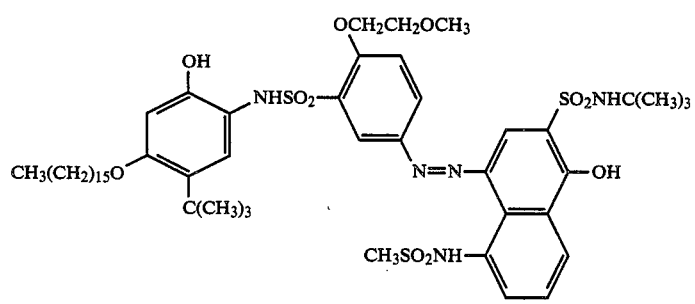 DRR-6
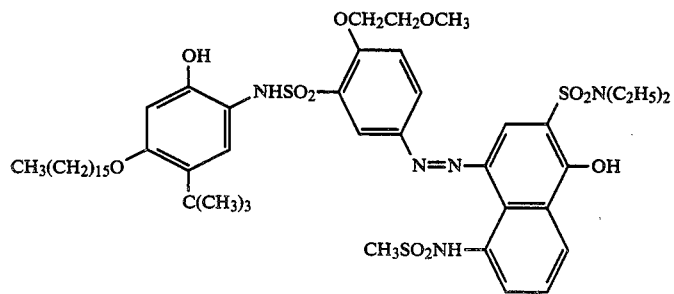 DRR-7
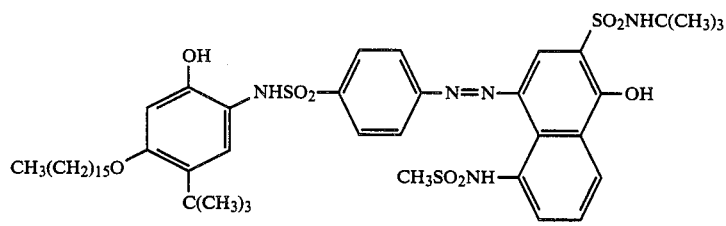

-continued
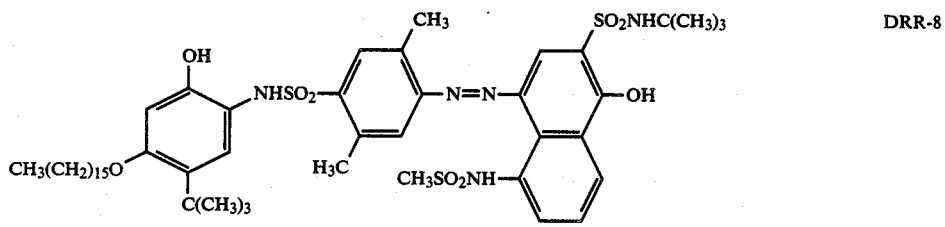 DRR-8
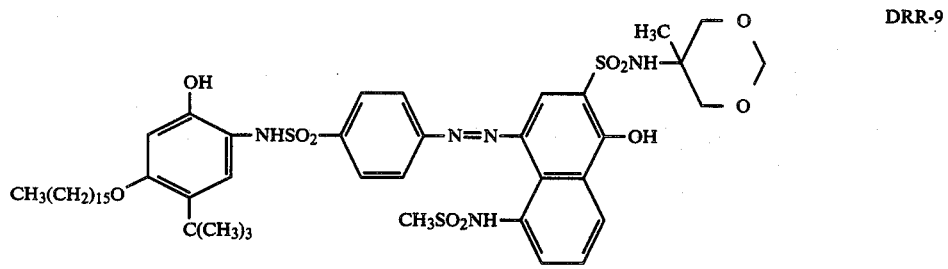 DRR-9
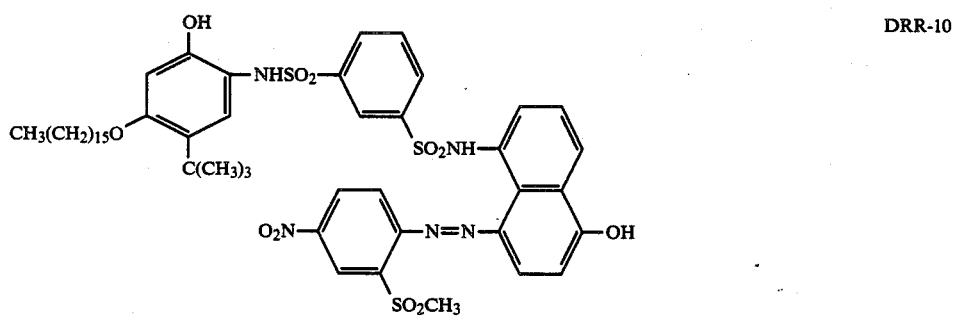 DRR-10
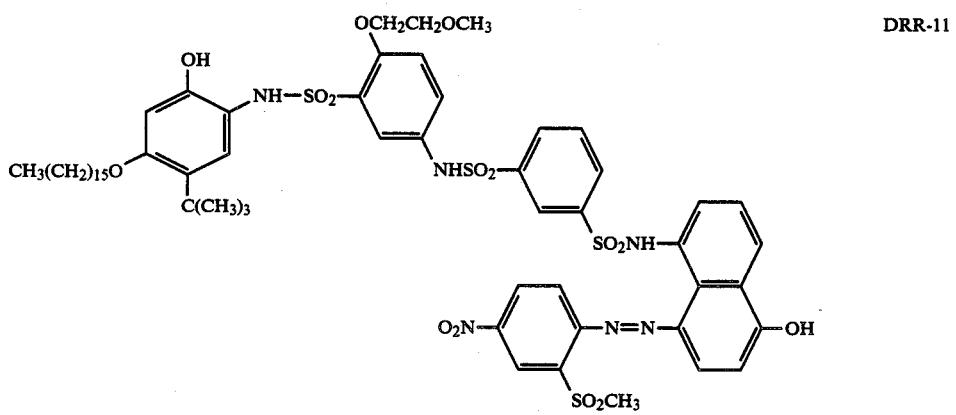 DRR-11
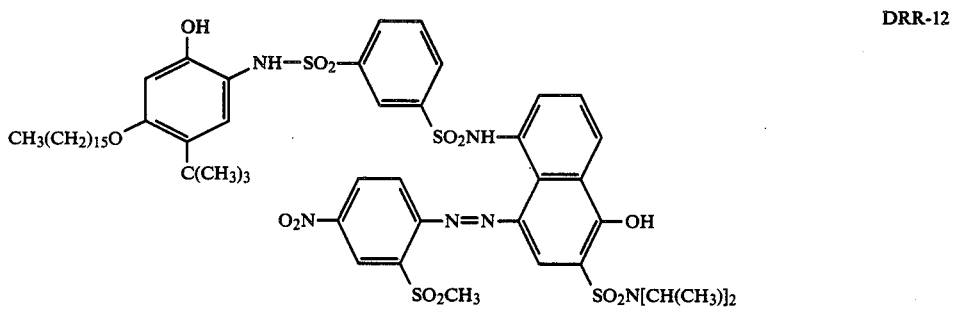 DRR-12

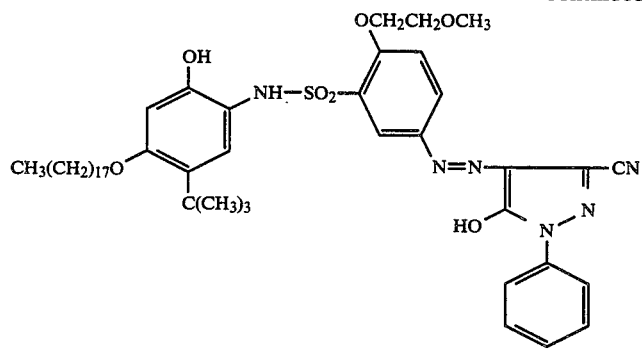
DRR-13
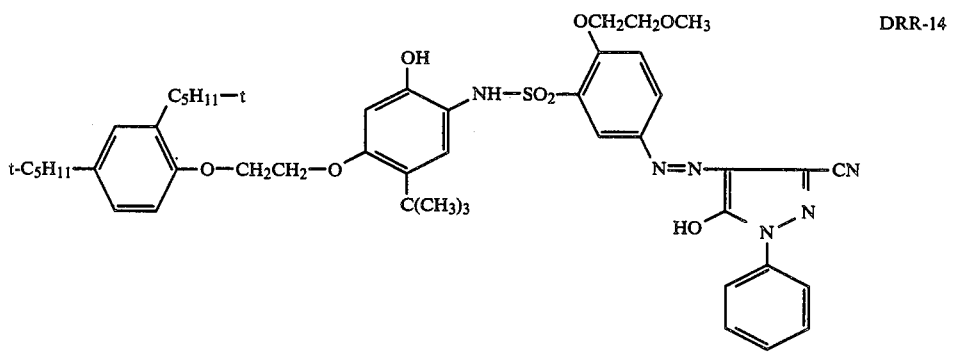
DRR-14
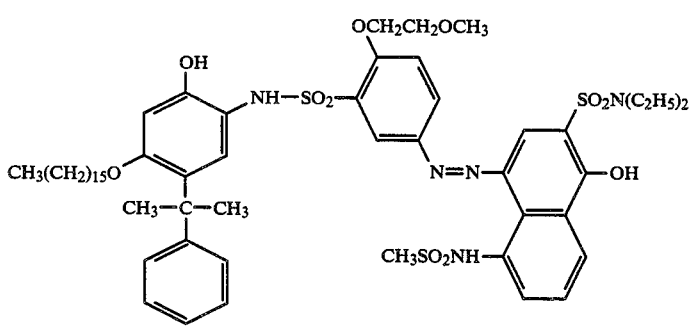
DRR-15
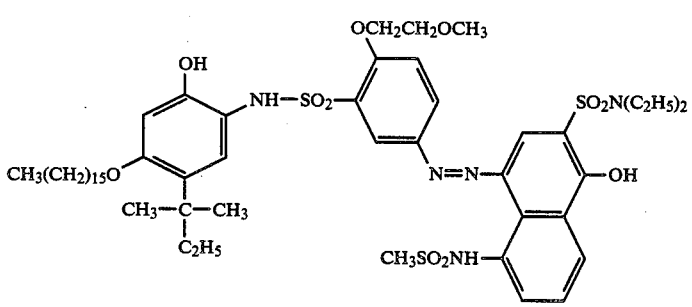
DRR-16
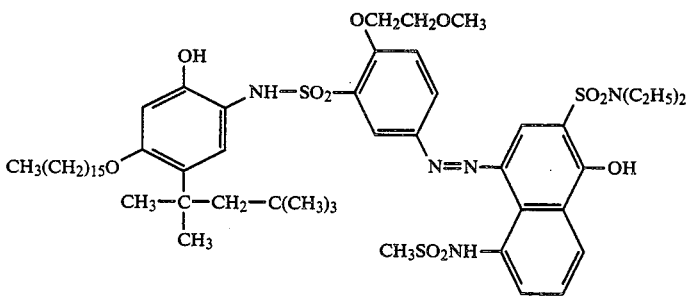
DRR-17

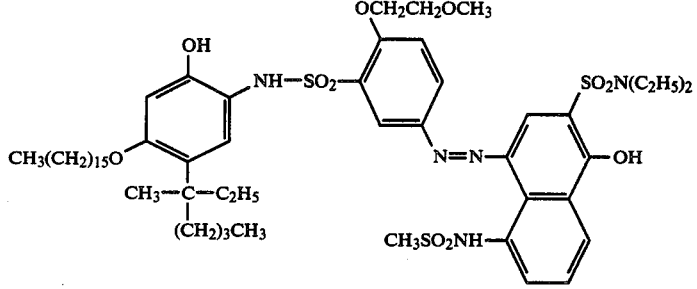
DRR-18
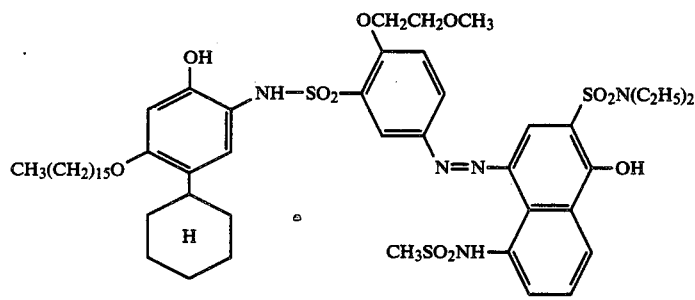
DRR-19
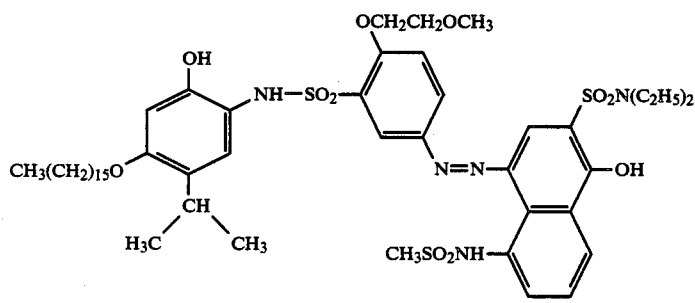
DRR-20
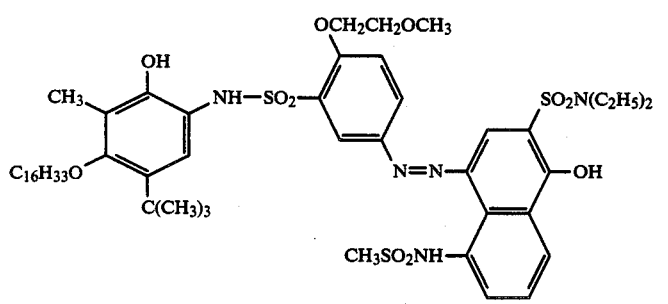
DRR-21
Preparation of the DRR compound represented by the general formula (XI) from the compound (I) of the present invention can be effected according to the following process:
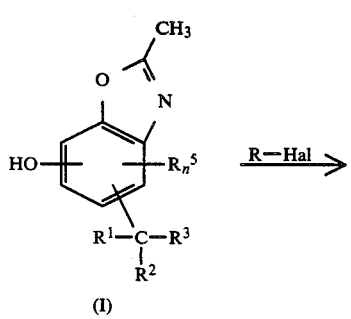
(I)
$\xrightarrow{R-Hal}$
-continued
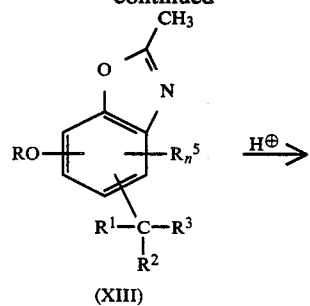
(XIII)
$\xrightarrow{H^{\oplus}}$

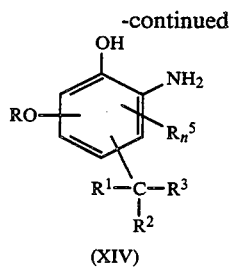 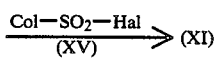

(XIV)

wherein Hal represents a halogen atom and other moieties have the same meanings as in the formula (XI).

Namely, in order to obtain compound (XIII) through O-alkylation of compound (I), R—Hal is used and, further, a basic material such as sodium alkoxide or potassium carbonate is used as a hydrogen halide extracting agent.

Next, compound (XIII) is treated with an acid such as diluted hydrochloric acid, whereby the oxazole ring is opened. Thus, compound (XIV) is obtained.

Methods for the synthesis of the dye moiety and its sulfonyl halide (XV) are described in Japanese Patent Application (OPI) Nos. 12581/73, 33826/73, 114424/74, 126332/74 and so on.

In general, it is preferred to conduct the condensation reaction of compound (XI) and compound (XV) in the presence of a basic material. Specific examples of such basic materials include hydroxides of alkali metals or alkaline earth metals (e.g., sodium hydroxide, potassium hydroxide, barium hydroxide, calcium hydroxide, etc.), aliphatic amines (e.g., triethylamine, etc.), aromatic amines (e.g., N,N-diethylaniline, etc.), heterocyclic aromatic amines (e.g., pyridine, quinoline, $\alpha$-, $\beta$- or $\gamma$-picoline, lutidine, collidine, 4-(N,N-dimethylamino)pyridine, etc.), and heterocyclic bases (e.g., 1,5-diazabicyclo[4,3,0]nonene-5, 1,8-diazabicyclo[5,4,0]undecene-7, etc.). In the case Hal=Cl, namely in the case that formula (XV) represents sulfonyl chloride, heterocyclic aromatic amines (particularly pyridine) are superior to other basic materials described above.

An example of the synthesis of a DRR compound using the intermediate of the present invention is illustrated in detail below.

REFERENCE EXAMPLE

Synthesis of Compound DRR-1

(a) Synthesis of 2-amino-4-t-butyl-5-hexadecyloxyphenol hydrochloride

In 30 ml of N,N-dimethylformamide were dissolved 10.5 g of 5-t-butyl-2-methyl-6-benzoxazole and 15 g of hexadecyl bromide. To the resulting solution, 10 g of potassium carbonate was added. The reaction mixture was stirred and heated to 90° C. Then, it was poured into ice water, and the oily material thus separated out was extracted with ethyl acetate. Anhydrous sodium sulfate was added to the resulting extract to dry the extract. The desiccated extract was filtered and concentrated. The thus obtained residue was dissolved in 120 ml of ethanol and 96 ml of 35% hydrochloric acid, and refluxed under heat. Crystals separated out and were recovered by filtration. Thus, 12 g of the above-described compound was obtained.

(b) Synthesis of Compound DRR-1

To 20 ml of N,N-dimethylacetoamide were added 4.4 g of 2-amino-4-t-butyl-5-hexadecyloxy-phenyl hydrochloride and 4.6 g of 3-cyano-4-(4-methoxyethoxy-5-chlorosulfonylphenylazo)-1-phenyl-5-pyrazolone. To the resulting mixed solution was dropwise added 4.7 ml of pyridine with stirring. After the conclusion of dropwise addition, stirring was continued for additional 2 hours at a room temperature. Then, 30 ml of methanol and 10 ml of water were added to the reaction mixture to result in the separation of an oily material. By the addition of about 20 ml of ethanol to the oily material, crystals separated out. The crystals were recovered by filtration. Yield 4.8 g.

While the invention has been described in detail and with reference to specific embodiments thereof, it will be apparent to one skilled in the art that various changes and modifications can be made therein without departing from the spirit and scope thereof.

What is claimed is:

1. A benzoxazole represented by formula (II)

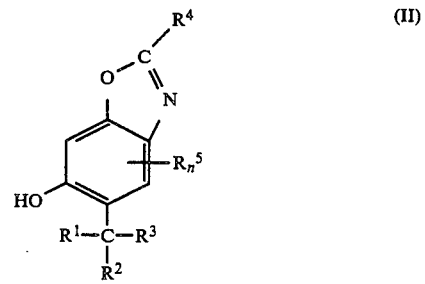

wherein $R^1$ and $R^2$ may be the same as or different from each other, and each represents an alkyl group of 1–24 C atoms, a substituted or unsubstituted phenyl group, a substituted or unsubstituted naphthyl group, or may combine to form a 5 to 20 membered ring; $R^3$ represents a hydrogen atom, an alkyl group of 1–24 C atoms, a substituted or unsubstituted phenyl group or a substituted or unsubstituted naphthyl group; $R^4$ represents an alkyl group of 1–40 C atoms; $R^5$ represents an alkyl group of 1–40 C atoms, an alkoxy group, or an alkylthio group wherein the alkyl moiety of said alkoxy or alkylthio group is 1–40 C atoms, a substituted or unsubstituted phenylthio group or a 1-phenyl-5-tetrazoyl-thio group, a halogen atom or an alkyl-CONH-group in which the alkyl moiety has from 1–24 C atoms, or a substituted or unsubstituted phenyl-CONH group, and n is 0, 1, or 2; the substituents of the substituted group of R, $R^2$, $R^3$ and $R^5$ being an alkoxy group, a cyano group, a hydroxy group, a nitro group, or an alkyl group, said benzoxazole derivative being useful as an intermediate for synthesis of an o-sulfanamidophenol derivative which acts as a dye releasing redox compound and provides a transferred dye image having high optical density when used in a diffusion transfer process.

2. A benzoxazole as in claim 1, wherein $R^3$ is an alkyl group of 1–24 C atoms, a substituted or unsubstituted phenyl group or a substituted or unsubstituted naphthyl group.

3. A benzoxazole as in claim 1, wherein $R^1$, $R^2$ and $R^3$ are alkyl groups of 1–24 C atoms.

* * * * *